US00PP21321P2

(12) United States Plant Patent
Khemakongkanond

(10) Patent No.: US PP21,321 P2
(45) Date of Patent: Sep. 28, 2010

(54) ***SCINDAPSUS* PLANT NAMED 'SUPHA10'**
(50) Latin Name: *Scindapsus pictus*
Varietal Denomination: SUPHA10

(76) Inventor: Kanchana Khemakongkanond, 57 Phattanakan Lane 63 Off 2, Bangkok (TH) 10250

( * ) Notice: Subject to any disclaimer, the term of this patent is extended or adjusted under 35 U.S.C. 154(b) by 0 days.

(21) Appl. No.: 12/455,716

(22) Filed: Jun. 6, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para

(57) ABSTRACT

A new and distinct *Scindapsus pictus* cultivar named 'SUPHA10' is disclosed, characterized by round, very dark green leaves. The new variety is a *Scindapsus*, and is normally used as an indoor ornamental plant.

1 Drawing Sheet

Figure 1:
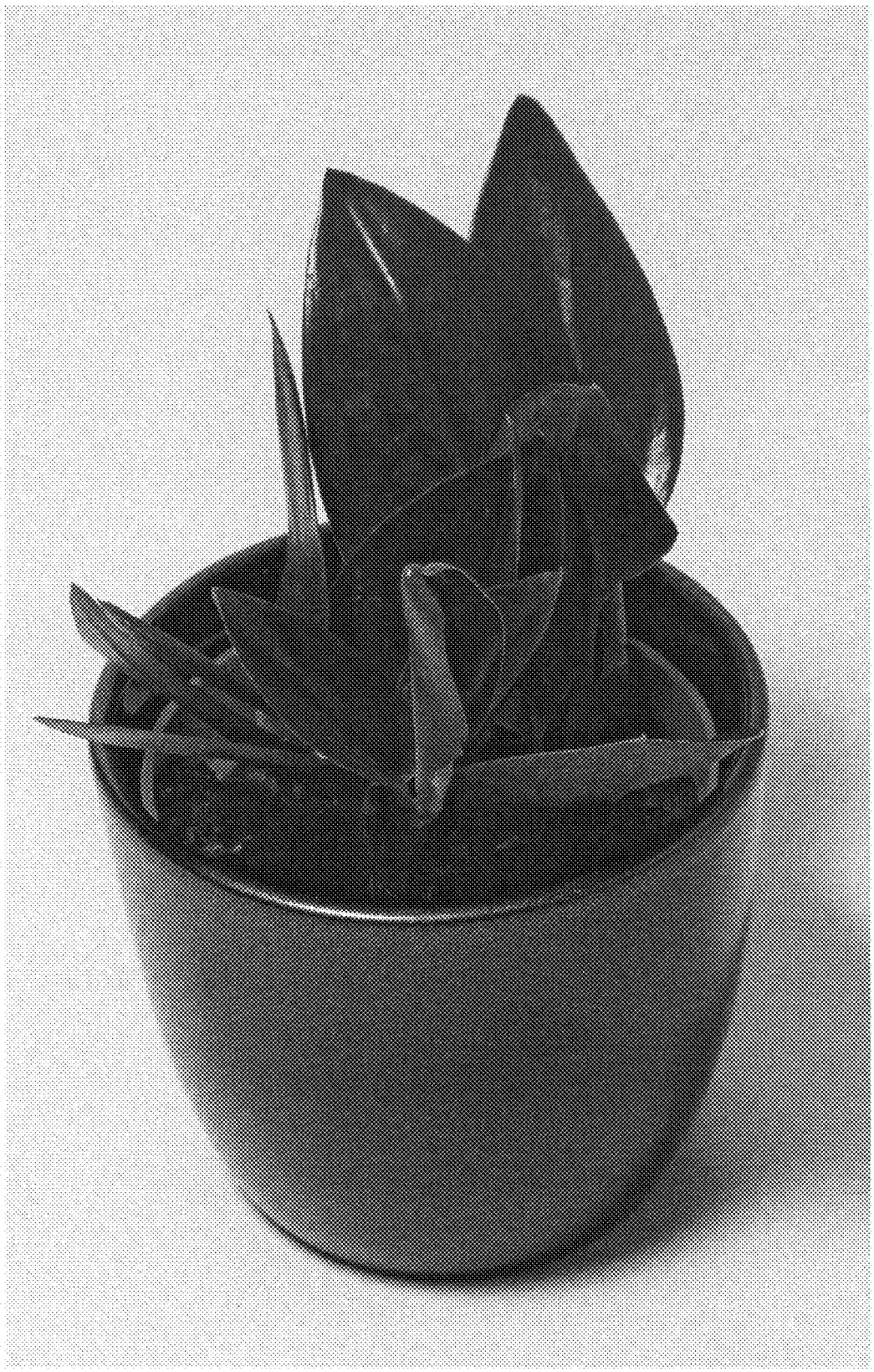

Latin name of the genus and species: *Scindapsus pictus*.
Variety denomination: 'SUPHA10'.

BACKGROUND OF THE INVENTION

The new cultivar was discovered as a chance, whole plant mutation in a commercial nursery in Chonburi, Thailand. The inventor, Kanchana Khemakongkanond, a citizen of Thailand, discovered the new variety as a whole plant mutation among several plants of the unpatented commercial variety, *Scindapsus pictus* 'Exotica.' The new variety was discovered during the Summer of 1999 by the inventor.

Asexual reproduction of the new cultivar 'SUPHA10' by vegetative cuttings was performed at a commercial nursery in Chonburi, Thailand during the Fall of 2000. Since that time, many generations have been reproduced, and have shown that the unique features of this cultivar are stable and reproduced true to type through successive generations.

SUMMARY OF THE INVENTION

The cultivar 'SUPHA10' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHA10.' These characteristics in combination distinguish 'SUPHA10' as a new and distinct *Scindapsus pictus* cultivar:

1. Compact plant shape.
2. Exceptionally dark green foliage.
3. Round, broad leaf morphology.

PARENT COMPARISON

Plants of the new cultivar 'SUPHA10' are similar to plants of the parent variety *Scindapsus pictus* 'Exotica' in most horticultural characteristics. However, plants of the new cultivar 'SUPHA10' produce wider leaves of a much darker color.

The parent variety is also the best commercial comparisons to the new cultivar.

BRIEF DESCRIPTION OF THE PHOTOGRAPH

The accompanying photograph in FIG. 1 illustrates in full color a typical plant of 'SUPHA10' grown in a greenhouse.

The pot size is a commercial 10.5 cm container. The plant shown is approximately 15 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'SUPHA10' plants grown in a commercial greenhouse in Honselersdijk, The Netherlands from early Winter to early Spring. The growing temperature ranged from approximately 20 to 21° C. at night and 20 to 22° C. during the day. Measurements and numerical values represent averages of typical flowering types. No chemical or photoperiodic treatments were given. The main stem of the plant was pinched at approximately 4 weeks after planning a rooted cutting.
Botanical classification: *Scindapsus pictus 'SUPHA*10.'

PROPAGATION

Time to Rooting: About 10 to 20 days at approximately 25° C.
Root Description: Small, fleshy, free-branching roots.

PLANT

Growth Habit: Upright, fleshy, very tender perennial, suitable for indoor ornamental use.
Height: Approximately 13.6 cm.
Plant Spread: Approximately 13.7 cm.
Growth Rate: Moderate. Approximately 8 to 10 cm per month while actively growing.
Branching Characteristics: One main stem, otherwise, weak basally branching.
Diameter of Stem: Approximately 0.3 cm.
Internode Length: Average 5.1 cm.
Texture of Stems: Rounded, smooth, moderately glossy.
Color of Stems: Near RHS Green 139A.
Stem strength: Moderate.
Number of Leaves per stem: Average 5.
Age of Plant Described: Approximately 20 weeks.
Pot size of Plant Described: 10.5 cm.

FOLIAGE

Leaf:

*Arrangement.*—Alternate, simple.
*Average Length.*—Approximately 10.7 cm.
*Average Width.*—Approximately 5.5 cm.
*Shape of blade.*—Broad ovate.
*Aspect.*—Young leaves slightly concave. Older leaves mainly flat.
*Apex.*—Acute.
*Base.*—Rounded.
*Attachment.*—Stalked.
*Margin.*—Entire.
*Texture of top surface.*—Smooth, glossy, leathery.
*Texture of bottom surface.*—Smooth, glossy, leathery.
*Color.*—Young foliage upper side: Darker than R.H.S. Yellow-Green 147A. Young foliage under side: Near RHS Greyed-Green N189B. Mature foliage upper side: Darker than R.H.S. Yellow-Green 147A. Mature foliage under side: Near RHS Greyed-Green 189A.
*Venation.*—Type: Pinnate. Color: Upperside: Near RHS 139A. Underside: Near R.H.S. Yellow-Green 147A.

Petiole:

*Length.*—Average 2.3 cm.
*Width.*—Average 0.3 cm.
*Coloration.*—Near RHS Greyed-Green 189A.

Other Characteristics: Aerial roots produced irregularly on main stem.

*Shape.*—Rounded, fleshy.
*Length.*—Approximately 0.2 cm.
*Diameter.*—Approximately 0.15 cm.
Texture.—Smooth, matte.
*Color.*—Near RHS Grey-Brown 199A.

FLOWER

Flowering not observed to date.

OTHER CHARACTERISTICS

Disease Resistance: Neither resistance nor susceptibility to diseases or pests normal to *Scindapsus* has been observed in this variety.

Drought Tolerance and Temperature Tolerance: Very tender perennial, low temperature damage occurs near 7°C. Tolerates high temperature to at least 40° C. No drought tolerance has been observed.

Fruit/Seed Production: Fruits and seeds have not been observed.

What is claimed is:

1. A new and distinct cultivar of *Scindapsus* plant named 'SUPHA10' as herein illustrated and described.

* * * * *